United States Patent [19]

Catsimpoolas et al.

[11] Patent Number: 4,769,362

[45] Date of Patent: Sep. 6, 1988

[54] INCREASED VASCULAR PERFUSION FOLLOWING ADMINISTRATION OF LIPIDS

[75] Inventors: Nicholas Catsimpoolas, Newton Centre; Robert McCluer, Acton; James Evans, Winchester, all of Mass.; Robert S. Sinn, New York, N.Y.

[73] Assignees: Trustees of Boston University, Boston, Mass.; Angio-Medical Corporation, New York, N.Y.

[21] Appl. No.: 852,444

[22] Filed: Apr. 14, 1986

Related U.S. Application Data

[63] Continuation-in-part of Ser. No. 782,724, Oct. 31, 1985, Pat. No. 4,710,490.

[51] Int. Cl.[4] .................................................. A61K 31/70
[52] U.S. Cl. .................................................. 514/25
[58] Field of Search .............................. 424/95; 514/25

[56] References Cited

U.S. PATENT DOCUMENTS

| | | | |
|---|---|---|---|
| 4,347,244 | 8/1982 | Mynard et al. | 514/25 |
| 4,456,596 | 6/1984 | Schafer | 514/25 |
| 4,476,119 | 10/1984 | Della Valle et al. | 514/25 |

FOREIGN PATENT DOCUMENTS

0146810 7/1985 European Pat. Off. .............. 514/25

*Primary Examiner*—J. R. Brown
*Assistant Examiner*—John W. Rollins, Jr.
*Attorney, Agent, or Firm*—Felfe & Lynch

[57] ABSTRACT

Lipid containing molecules and compositions, including gangliosides and omental tissue extracts had previously been found to be effective in increasing angiogenesis. It has now been found that these same materials cause increased localized perfusion in mammals. A method for providing increased perfusion, using these compositions, is presented herein.

15 Claims, 7 Drawing Sheets

INCREASED VASCULAR PERFUSION FOLLOWING ADMINISTRATION OF LIPIDS

This is a continuation-in-part of U.S. application Ser. No. 782,724, filed Oct. 31, 1985.

FIELD OF THE INVENTION

This invention relates to a method of stimulating angiogenesis and increased blood perfusion in mammals by treatment with substances which are effective to bring about said angiogenesis and increased blood perfusion.

BACKGROUND AND PRIOR ART

In applicant's co-pending parent application, Ser. No. 782,724, now U.S. Pat. No. 4,710,490 the disclosure of which is incorporated by reference herein, compositions which exhibited efficacy in causing angiogenesis were described. Among the tests which showed such efficacy were CAM assays, involving live chick embryos. This application alluded to co-pending application Ser. No. 642,624, filed Aug. 20, 1984, now U.S. Pat. No. 4,199,788, the disclosure of which is also incorporated by reference herein. This application discloses an animal model (the "cat leg" model) which was used to demonstrate in vivo efficacy of a chloroform/methanol fraction of an omental tissue extract. The "cat leg" model which is described therein, is the animal model described in th Detailed Description of Preferred Embodiments which follows, infra.

The omentum was reported to be effective in supplying blood to ischemic areas of the body as early as 1903. See, e.g. DeRenzi, et al., *Berl. Klin. Woch.* 40:773-775 (1903); Morrison, *Brit. Med. J.* 1:76-78 (1906); Wilkie, *Brit. Med. J.* 2:1103-1106 (1911). Later work, e.g., O'Shaughnessy, *Brit. J. Surg.* 23:665-670 (1936); Knock, *Surg. Form.* 9:230-232 (1958), shows that predicted omentum might provide collateral circulation to the heart. Later work by Vineberg and associates, *Can. Med. Assoc. J.* 87:1074-1076 (1962); *Can. Med. Assoc. J.* 90:717-722 (1964); *Am. Heart J.* 72:79-93 (1966); *Dis. Chest.* 54:315-322 (1968); Surgery, *Gynecol. Obstetrics* 137:564-578 (1973), reported treatment of patients with coronary/artery disease in which direct myocardial implantation of the internal mammary artery with pericoronary omental strips.

Current interest has centered around using the omentum for revascularization of the central nervous system. For example, Goldsmith, et al., *Surgery* 88:732-736 (1980); *Stroke* 9:224-229 (1978); *Am. J. Surg.* 130:317-320 (1975); *Am. J. Surg.* 129:263-265 (1975); *Arch. Surg.* 106:695-698 (1973); *Rev. Surg.* 24:379-380 (1967) have shown that vascularization occurs at an omental cerebral and omental spinal cord interface which allows for the addition of an extensive new cource of blood to the brain and spinal cord, in spite of the absence of ischemia in these organs. Following this, Goldsmith, et al., *JAMA* 252:2034-2036 discovered an omental lipid fraction which possesses patent angiogenic activity.

Folch, et al., *J. Biol. Chem* 226:497-509 (1957) teach a method for isolating and purifying lipids in animal tissue. References to "Folch fractions" and "Folch apparatus" made herein refer to the methods set forth in this paper. Ledden, et al., *Meth. Enzym.* 83:119-139 (1982) teach the isolation and analysis of gangliosides in general, while Williams, et al., *J. Neurochem.* 35:226-269 (1980) show the use of C18 cartridges during ganglioside isolation. Kannagi, et al., *J. biol. Chem.* 257:14,865-14,874 (1982) show that glycosphingolipids of human erythrocytes react with monoclonal antibodies to developmental antigen SSEA-1

None of the prior art has taught or suggested, however, that localized vascular perfusion could be obtained using omental lipid materials, or other lipid material. Localized vascular perfusion to traumatized tissue is desirable. While the site of such perfusion decrease is sometimes easily detectable, frequently it is not. Additionally, sometimes, while the site of reduced perfusion is detectable, application of a circulation or perfusion enhancing drug locally is difficult. Material which increases perfusion systemically is clearly not desirable in many cases, as will be immediately apparent to one skilled in the art.

Hence, it is an object of this invention to provide compositions useful in increasing localized perfusion to traumatized tissue in mammals.

It is a further object of this invention to provide a method of increasing perfusion, using said composition.

It is a further object of the invention to present a method for delivery of said compositions to particular sites of traumatized tissue for increased localized perfusion, using systemic applications.

How these and other objects of the invention are accomplished will be readily ascertained by review of the materials which now follow.

BRIEF DESCRIPTION OF THE FIGURES

FIG. 2: Examples of radionuclear imaging of the hind limbs of the cat. Note that the X-axis transverses both limbs (right and left) and the radioactive counts are displayed as separate peaks for its limb. Integration of the peaks—after deconvolution—produces a quantitative means to compare the radiodensity in the two limbs at acerta in transverse section. The X-axis is then moved to another section (see A, B, C, D) and the process is repeated. FIG. 3 below shows a composite profile of ten sections. NOTE: This cat was given i.m.injections of the angiogenic lipid material at a location remote to the wound site daily. Nuclearscans were taken at day 3.

FIG. 7: Radiodensity ratio distributions (Gaussian of day 7 post-operative animals injected i.m. in the wound area with porcine omentum neutral lipids and with an 1000:1 (w/w) mixture of porcine omentum neutral lipids and fetal calf brain gangliosides.

DETAILED DESCRIPTION OF PREFERRED EMBODIMENTS

Figure 1:
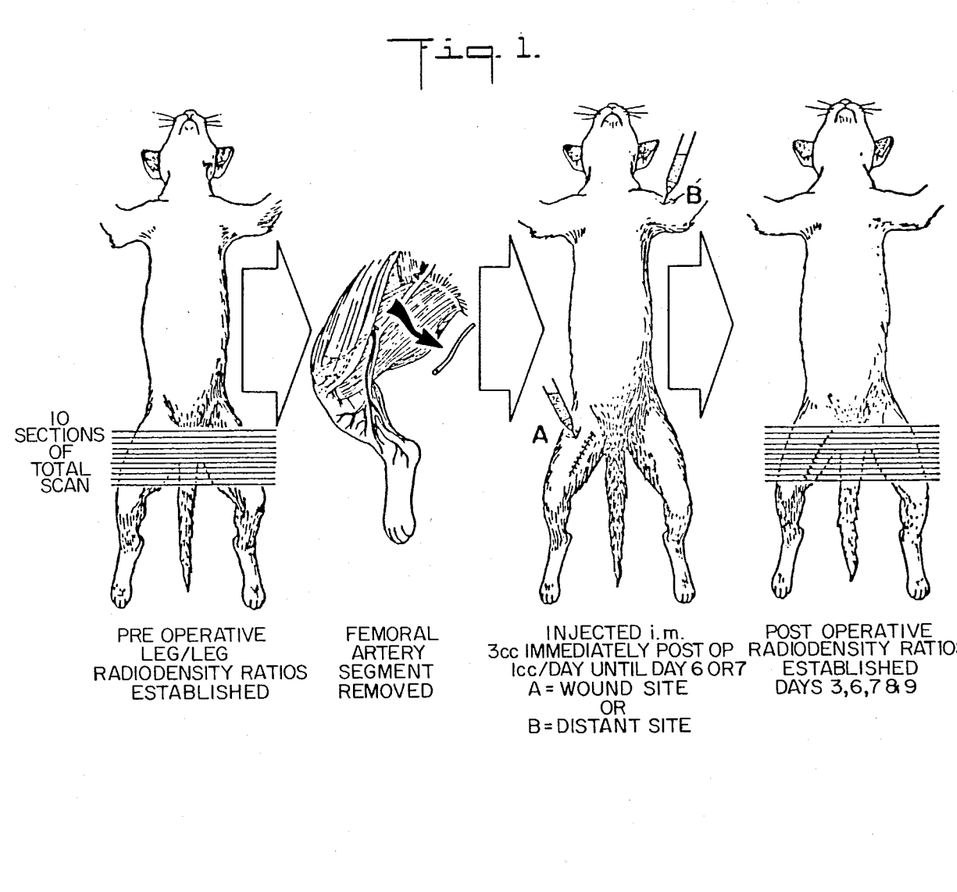
FIG. 1: Composite drawing of experimental design. The second image from the left represents an anatomical diagram of the hind limb of the cat showing the excised part of the femoral artery and ligations at the inguinal crease and Hunter's canal.
Figure 2A:
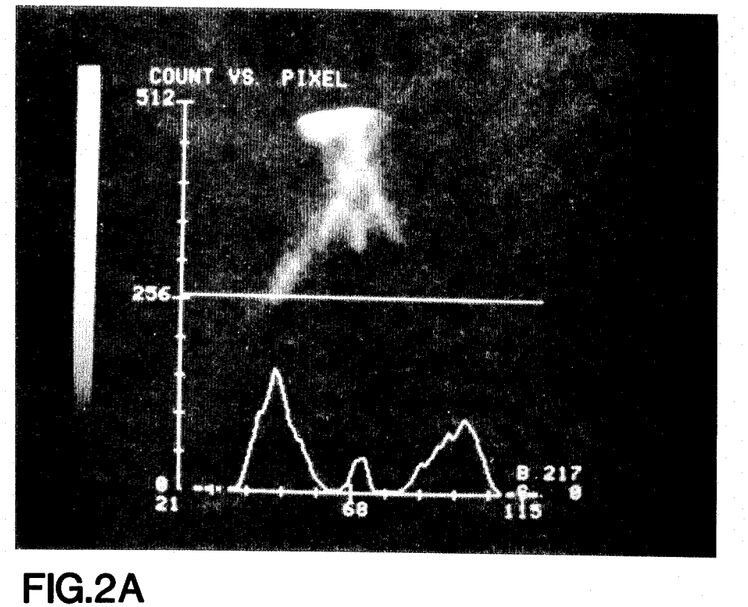
Figure 2B:
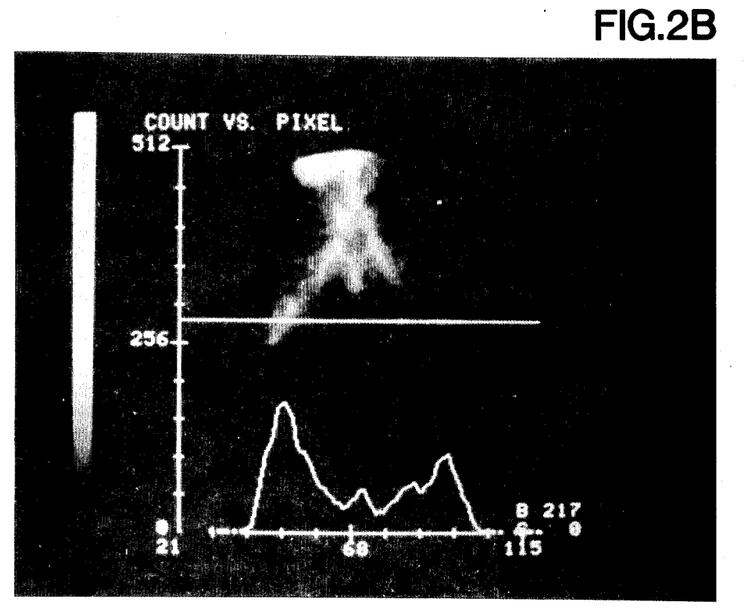
Figure 2C:
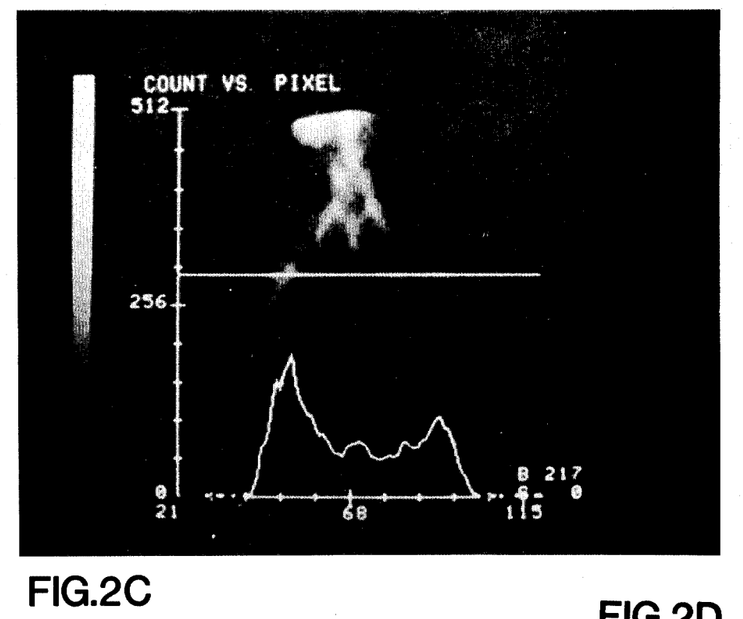
Figure 2D:
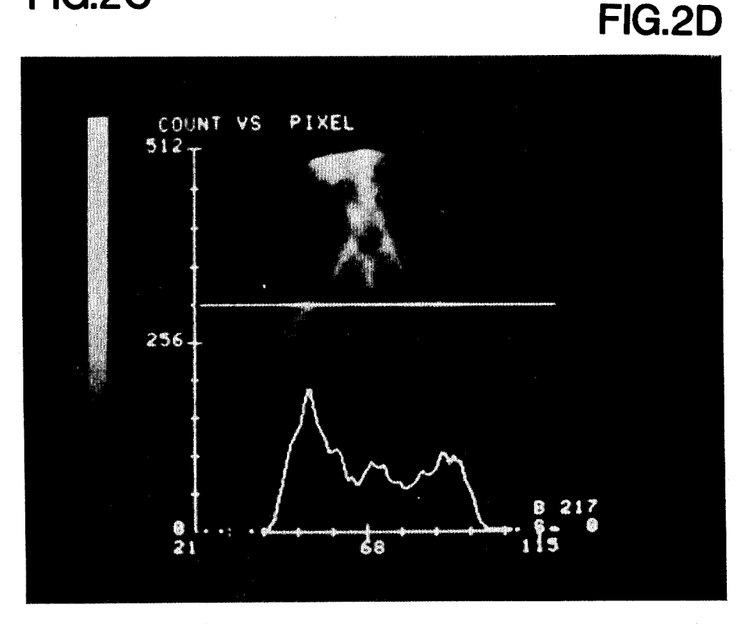

A need for localized tissue revascularization was created by surgically excising a prescribed segment of the femoral artery in a hind limb of a cat (FIG. 1). The lipid materials, or control material (saline), were injected intramuscularly into and around the wound (hind limb), or at a distant site (front limb). The distant site injections were administered to learn whether the lipid materials could exert their effect by being absorbed into the general circulation with subsequent increased vascular perfusion developing at the wound site. Targeting of traumatized tissue to effect localized increased perfusion, using systemic application, was studied as well.

The experiment involved four major steps: (1) Preparation of the lipid materials; (2) creation of a standardized surgical wound resulting in a need for increased blood supply; (3) injection of the lipid material or saline; (4) pre- and post-operative nuclear imaging procedures to demonstrate differences in vascular perfusion.

Preparation of Omental Lipid Fractions

The technique for preparing the chloroform/methanol fraction CMFr has been described in co-pending application and is now briefly outlined. Adult cats weighing 2.5 to 3.0 kg were anesthetized by an intramuscular injection of ketamine (7.0 mg/kg) following which a laparotomy was performed through a midline incision. At this point, the omentum was surgically removed and placed in a plastic bag previously cooled to 4° C. The omentum was weighed (range 30-60 g) and spread on a plastic surface where it was cut into pieces approximately 4 cm$^2$ followed by placement in a Waring blender containing 30 ml of phosphate buffered saline (PBS); the Waring blender and the solutions being previously pre-cooled to 4° C. Homogenization was performed for five minuted at 20,000 RPM. THe resulting homogenate was centrifuged for 20 minutes in 250 ml plastic bottles at 1600 g in a centrifuge refrigerated to 4° C. Following centrifugation, three fractions were visible in the bottles; i.e., a pellet, a turbid homogenate, and a floating cream-colored lipid cake. The lipid cake was removed after decantation of the homogenate and weighed following which it was homogenized in a Waring blender for two minutes with chloroform/methanol solvent (2/1:v/v) at room temperature at a ratio of one gram of lipid cake to 10 ml of solvent. Particulate matter was removed by centrifuging at 200 g at 4° C. for ten minutes. The resulting clear supernatant was then subjected to rotary evaporation at 37° C., under vacuum to remove the solvents. The fatty material that remained was called the chloroform/methanol lipid fraction (CMFr). The material was stored at −20° C.

Other Lipid Preparations

CMFr from Porcine omentum was prepared as above and was dissolved in hexane (approx. 60 ml hexane for every 10 g of CMFr) and 0.66 volumes of 95% ethanol were added. The phases were mixed thoroughly and were allowed to separate. The upper phase (hexane) was reextracted with 95% ethanol and the resulting lower phase of the re-extraction was combined with the first ethanol fraction. The combined ethanol fractions were also re-extracted with hexane, and the resulting hexane layer was combined with the first hexane fraction. The hexane solvent was evaporated in vacuo to produce the "porcine omentum neutral lipids" (PONL) used in these experiments.

Bovine brain monosialo—(GM1) disialo—$_\Lambda$(GD1a) and trisialo—$_\Lambda$(GT1) angliosides were purchased from Supelco and mixed in the ratio described below. The trisialoganglioside GT1b contains 10-30% GD1b.

Fetal calf brains of fetal age 6 months or less were used for the isolation of gangliosides. The fetal calf brains were rinsed with saline and the meninges carefully removed. The brains were then homogenized in three volumes of cold acetone. The homogenate was filtered and the residue again extracted with 3 volumes of cold acetone. Following filtration the residue was extracted according to the method of Kannagi et al. (1982). The residue was homogenized in 3 volumes of isopropanol-hexane-water, 55:20:25, and allowed to stir overnight at room temperature. The homogenate was filtered and the residue re-extracted with 3 volumes of the same solvent mixture. This was again filtered and the two filtrates combined and dried by rotary evaporation. The lipid residue was dissolved in chloroform-methanol, 2:1 and partitioned according to the method of Folch et al. (1957), by adding one-fifth volume of water and mixing thoroughly. The upper phase was removed and the lower phase re-extracted 2 times using theoretical upper phase, choloroform-methanol-water (3:48:47).

The upper phase was brought to a final concentration of 0.1M KCl and applied to a reverse phase C18 column according to the method of Williams and McCluer (1980). After desalting the gangliosides were eluted from the column using methanol. The sample was taken to dryness and treated with 0.3M then neutralized with acetic acid and desalted again using the C18 column described above. The methanol fraction containing neutral and acidic glycosphingolipids was taken to dryness.

Neutral glycosphingolipids and gangliosides were separated using ion exchange chromatography. The mixture was dissolved in methanol and applied to a DEAE-Sephadex column as described by Ledeen and Yu (1982). Neutral glycolipids were eluted using three volumes of methanol. The total ganglioside mixture was eluted from the anion exchange resin with 0.5M ammonium acetate in methanol. The ganglioside fraction was taken to dryness and again desalted as described above.

This fraction was redissolved in methanol and an aliquot applied to a Merck HPTLC plate and developed using choloroform-methanol-0.25% CaCl2 (55:45:10). The gangliosides were visualized with resorcinol reagent. The major components of this mixture are GD1a, GT1b, GM1, GD1b, GD3, GM2, GM3 and GQ.

Creation of Standardized Wound

Cats of both sexes were anesthetized with intraperitoneal injection of sodium pentobarbitol (33 mg/kg). After the animals were anesthetized, a longitudinal skin incision was made in a single hind limb extending from the inguinal crease to the lower portion of the thigh over the femoral vessels. The right or the left hind limbs were alternately operated upon in successive animals during this experiment.

A segment of femoral artery was removed from the inguinal crease to the bifurcation of the femoral artery at the lower end of Hunter's Canal. The divided ends of the femoral artery were ligated with 3-0 silk suture material. The wound was then irrigated with saline followed by loose closure of muscle overlying the divided femoral artery using a running 3-0 chromic catgut suture. The skin was approximated with interrupted 3-0 silk sutures. The femoral artery in the unoperated limb served as the basis for a comparison of nuclear imaging of vascular perfusion.

Injection of lipid Fractions

The lipid fractions were injected intramuscularly using a #19 gauge needle. The injected material was warmed to 37° C. immediately prior to administration in order to lower the viscosity of the substance which facilitated its passage through the hypodermic syringe and needle. In some cats the intramuscular injections were made in and around the area of the excision whereas in other animals injections were made i.m. in a front limb. Approximately 3 cc of lipid fractions as such or dissolved in PBS (see details under results) were initially injected followed by injections of 1 cc/day for six or seven days. Control cats received intramuscular injections of saline in a manner identical to the administration of the lipid material. Additional cats who had not been subjected to an surgery had omental lipid material injected into the thigh muscles adjacent to an unoperated femoral artery in order to learn if the injected lipid material stimulated vascular perfusion in the absence of a wound.

Nuclear Imaging Procedures

Regional vascular perfusion of the hind limbs in this experiment was demonstrated by tagging red blood cells of the cats with Technetium (Tc-99) with subsequent imaging on a gamma camera coupled to a computer. Nuclear imaging of the hind limbs of the animals was done on day 0 (immediately prior to femoral artery segment removal) and on postoperative days 3, 6, 7, and 9. Some cats had nuclear scans on all of these days, but due to logistics, scheduling, and technical computer difficulties, scanning on each of these days was not possible in every cat. However, nuclear imaging of the animals on prescribed days was not a requirement in this experiment since results were based on the mean ratio (R) of vascular perfusion of one leg in comparison to the other leg; a ratio which would be valid at any point in time.

Figure 3:
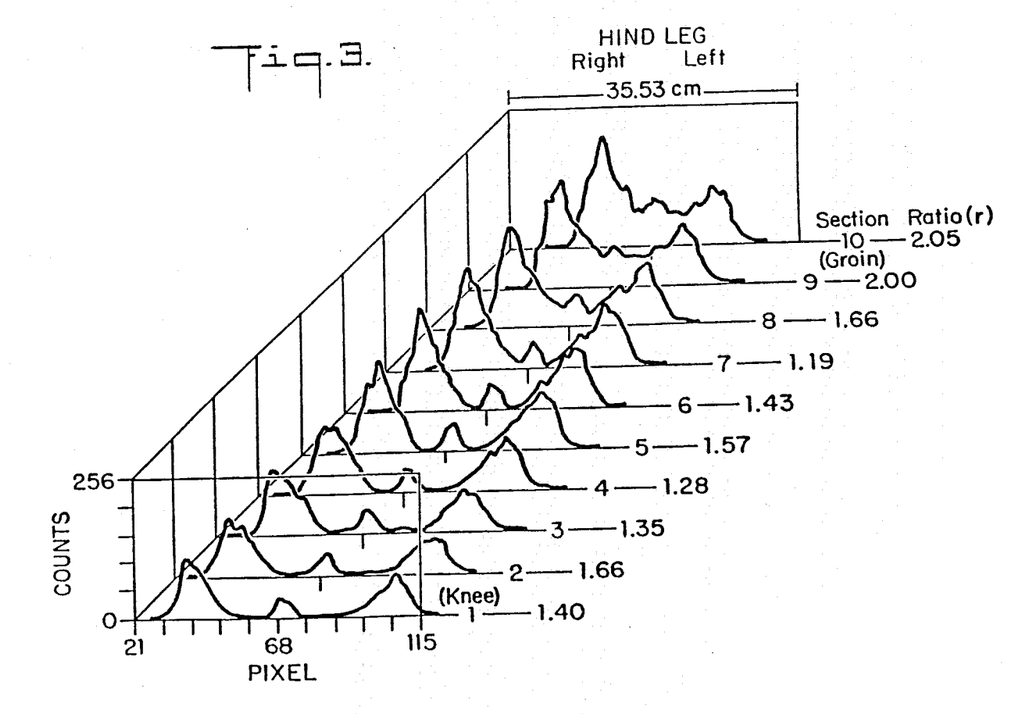
FIG. 3: Composite radiodensity profiles of ten sections of the cat limbs obtained as shown in FIG. 2. The area of the peaks corresponding to the right and left limbs as well as the ratio of the right (operated) limbs is displayed. Statistical analysis of the values of all ten sections produces the mean R value (±one standard deviation) shown under "results."

The cats were anesthetized by an intraperitoneal injection of sodium pentobarbitol (33 mg/kg). In preparation for nuclear imaging, a small skin incision was made in a front limb in order to expose a vein suitable for intravenous injection of 500 mg of stannous ion administered as stannous pyrophosphate (pyrolite). Twenty minutes later, 10 mCi of Technetium (Tc-99) was injected intravenously. Immediately after the Tc-99 injection, the animals were imaged anteriorly and posteriorly using a gamma camera interfaced with a computer system. Each ( scanning image of the legs ($5\times10^6$ accumulated counts per image) was stored for later data retrieval and analysis. Upon retrieval, each image was analyzed using "region of interest" techniques by means of a computer program (FIG. 2) which determined count data along orthogonal axis. The X-axis traversed both hind limbs and the counts (Y-axis) were displayed in the form of a radiodensity profile along a narrow (3 pixel) horizontal channel. The area of each peak representing the total counts for a particular section of the right and left hind limbs was integrated and the sectional ratio (r) of comparable areas of the surgically operated vs. the non-operated limb was computed for each of the sections. Ten such radiodensity profiles were obtained of equidistant sections from each hind limb and the mean R ($\pm$standard deviation) for each scan was compiled from the sectional (r) values (FIG. 3). The resulting mean (R) values derived from each radiodensity profile formed the basis for evaluating the efficiency of injected omental lipid factor as compared to controls; the radiodensity being a direct reflection of the vascular perfusion present in the lower limbs.

RESULTS AND DISCUSSION

The mean ration (R$\pm$standard deviation) of the radiodensity profile of the hind limbs reflected regional vascular perfusion of the respective extremity. A mean ratio (R) of 1.00 indicated equal radiodensity between the two hind limbs and thus equal vascular perfusion. Conversely a mean ratio (R) above or below 1.00 indicated an elevated or decreased vascular perfusion of a limb in comparison to the opposite extremity.

Pre-Operative Baseline Study

The mean ratio ($\overline{R}$) of the radiodensity profiles of the hind limbs of the cats taken at day 0 (immediately pre-operatively) was $1.045\pm0.11$. This figure was based on 16 cats whose radiodensity profiles demonstrated the close similarity of vascular perfusion existing between individual hind limbs (FIG. 4).

Post-Operative Baseline Study

Figure 4:
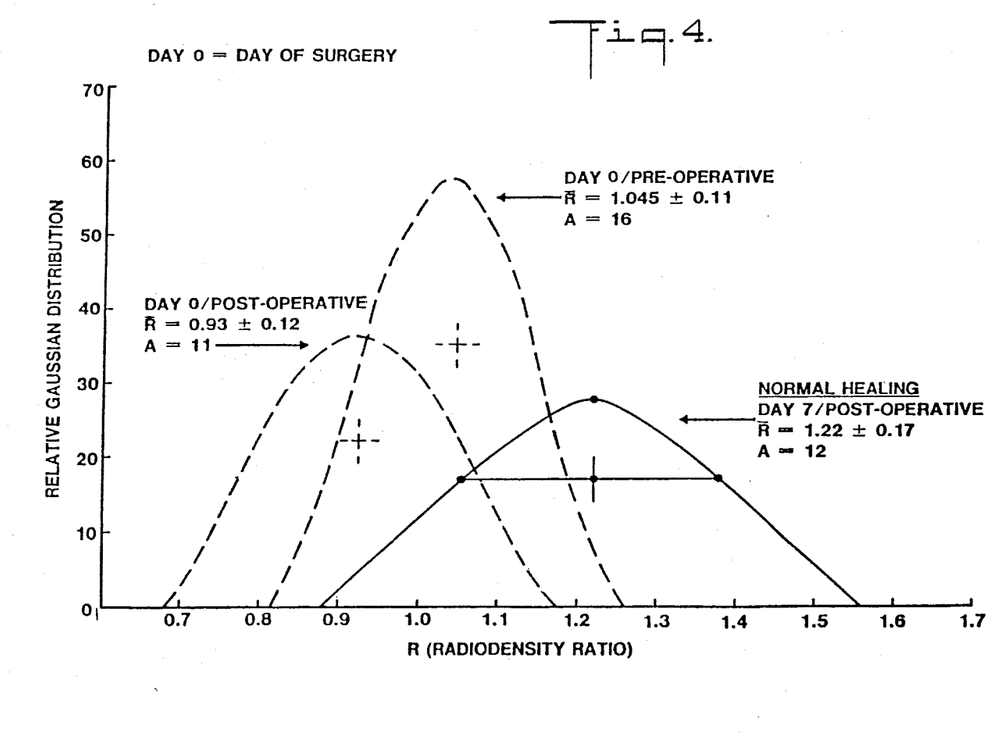
FIG. 4: Radiodensity ratio distributions of day zero pre-operative and post-operative animals, and of operated animals allowed to heal for seven days without any injections of lipid material. (R=mean ratio of all animals; A=number of animals). The solid horizontal bars signify ±one standard deviation.

The mean ratio $\overline{R}$ taken at day 0 immediately post-operatively was $0.93\pm0.12$ (FIG. 4). Eleven animals were involved in this study. It, thus, appears that the surgical removal of the femoral artery segment results in somewhat reduced regional blood perfusion, as expected.

Normal Healing

Twelve animals were operated and allowed to heal for seven days without injections of any material at all. The results of FIG. 4 show that the mean ratio R for these animals was $1.22\pm0.17$. This indicates that the normal healing process involves an increased blood perfusion in the region of operation.

Feline CMFr Injections

Twelve cats comprised this group; six animals received intramuscular injection of omental lipid material and six control cats received intramuscular injections of saline. The mean ratio $\overline{R}$ of the radiodensity profiles of animals nuclear imaged on days three, six, and nine was $1.81\pm0.30$ in those who received intramuscular injections of feline omental lipid CMFr material as compared to a mean ratio $\overline{R}$ of $1.16\pm0.18$ in the cats who received intramuscular injections of saline. This difference was of high statistical significance ($P<0.001$) using the statistical method of one-way analysis of variance and t-test.

Figure 5:
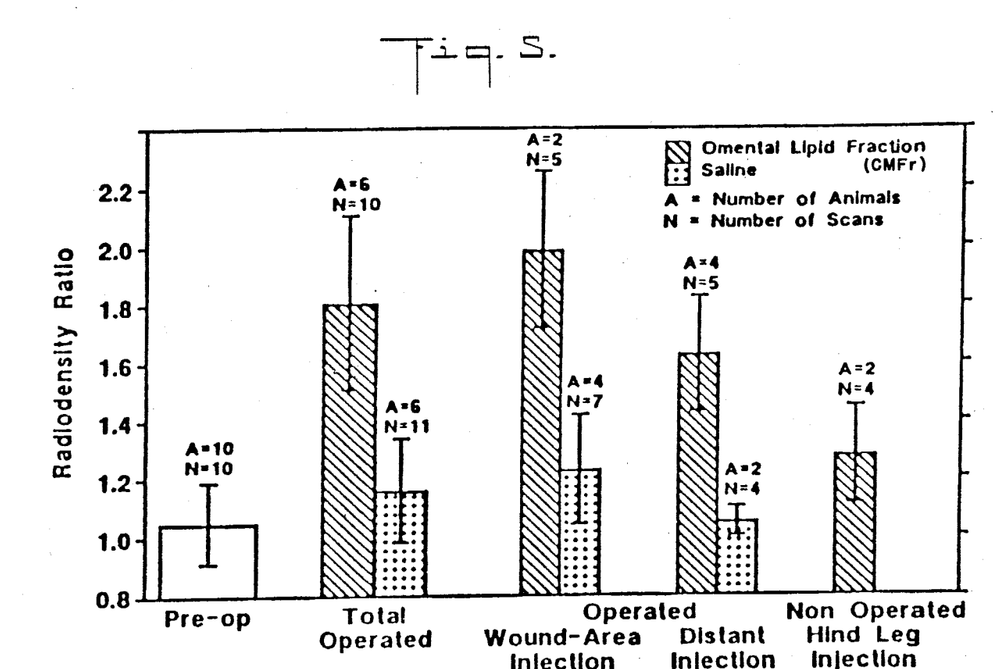
FIG. 5: Radiodensity data of animals injected with feline omentum CMFr or saline (control).

For further evaluation of the data the animals were subdivided into the following groups: animals who received intramuscular injections directly into the wound (wound area injection group) and those who received injections at a site far distant from the wound (distant injection group). FIG. 5 depicts the results set forth infra, and which now follow.

(a) Wound Area Injection Group: Intramuscular injections of the omental lipid CMFr fraction into the area of the femoral artery wound caused a considerable increase in vascular perfusion as evidenced by greatly increased radiodensity ratios. The mean ratio $\bar{R}$ of animals injected with feline CMFr was $1.99\pm0.27$, as reported supra whereas control cats who had saline injected into the wound site showed a mean ratio $\bar{R}$ of $1.23\pm0.19$, an increase of 62%. The difference between these ratios was of high statistical significance ($P<0.001$)

It should be noted that the mean ratio $\bar{R}$ of the saline injection animals as reported supra ($1.23\pm0.19$) was higher than the pre-operative mean ratio ($\bar{R}$) of normal (unoperated) limbs which was $1.05\pm0.14$, by almost 17%. This increase in the mean ratio ($\bar{R}$) in the saline injected cats was attributed to the surgical wound undergoing daily irritation from the frequent intramuscular injections into the wound site.

(b) Distant Injection Group: Animals that received intramuscular injections of omental CMFr into a front limb which was far distant from the surgical wound in a lower limb showed considerable increase in radiodensity (vascular perfusion at the wound site) with a mean ratio ($\bar{R}$) of $1.63\pm0.20$ compared to a mean ratio ($\bar{R}$) of $1.05\pm0.05$ in the animals who had saline injected in a front limb ($P<0.001$). This represents an increase of 55%. This ability of omental lipid material to cause increased vascular perfusion at a wound site far distant from its intramuscular injection into a front limb strongly suggested that the omental substance is absorbed into the systemic circulation and causes its reaction directly within the injury site.

It is observed that the percentage increase is approximately the same for both cases (a) and (b).

(c) Injection Into Normal Areas: Cats who had omental lipid material injected into and around the muscular area surrounding an unoperated femoral artery showed only a slight increase in radiodensity in the area of the injection ($1.28\pm017$). This figure was comparable to the radiodensity which followed saline injection into the area surrounding segmental femoral artery excision ($1.23\pm0.19$). This information indicated that the effectiveness of omental lipid material is enhanced whe administered in the presence of a healing wound.

In both cases (b) and (c), it is essential to note that targeting of traumatized tissue by systemic application was achieved. Further, no activity was observed at the injection site with any other non-traumatized tissue.

Effect of Ganglioside Mixtures

Figure 6:
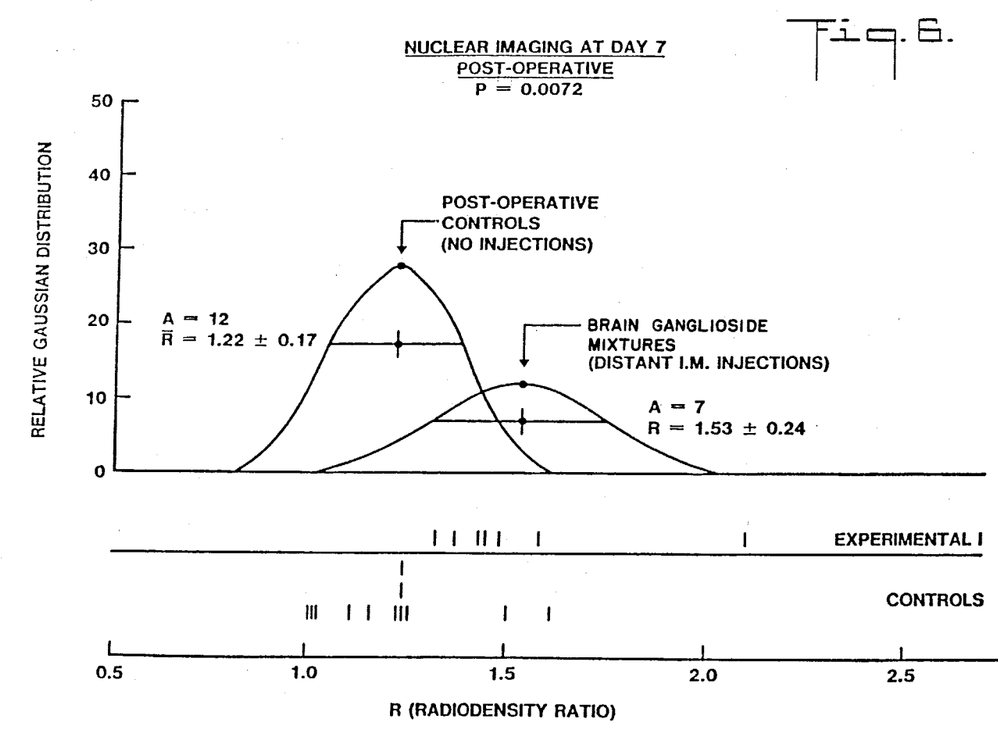
FIG. 6: Radiodensity ratio distributions in day 7 post-operative animals injected i.m. (distantly to the wound) with brain ganglioside mixtures (as shown in Table 1) and in normally healing animals (no injections). The solid horizontal bars signify ±one standard deviation.

Feline omentum CMFr contains gangliosides. It was, therefore, interesting to examine the effect of this class of compounds on the blood perfusion characteristics of operated animals. Table 1 shows the mixtures of fetal calf brain (prepared as described supra) and bovine brain (obtained from Supelco) gangliosides and the total amounts injected over a six-day period. Each material listed in Table 1 was administered to a subject animal. The figures given for R($+$S.D.) represent the mean of seventy scans (10 per animal) performed on each animal. The gangliosides were dissolved in phosphate buffered saline (PBS) and were injected i.m. distant to the wound area daily for six days. The animals were radioimaged at day 7 post-operatively. All the gangliosides mixtures produced R values which were higher than in normally healing animals (see Table 1). FIG. 6 demonstrates graphically the distribution of R values between the normally healing cats and the one injected with the mixtures of gangliosides. The P value for the two groups was 0.0072.

TABLE 1

Effect of Fetal Calf Brain and Bovine Brain Ganglioside Mixtures on the Regional Blood Perfusion of Operated Animals. The Gangliosides were Injected Distant to the Wound.

| Material | Amount (mg) | R($+$S.D) |
|---|---|---|
| Fetal calf brain gangliosides (Di/Tri) | 10 | $1.43\pm0.40$ |
| Fetal calf brain gangliosides (Di/Tri) | 30 | $1.58\pm0.18$ |
| Bovine Brain | | |
| Mixture of disialoganglioside and trisialoganglioside (1:2 w/w) | 10 | $1.48\pm0.37$ |
| Mixture of disialoganglioside and trisialoganglioside (1:2 w/w) | 15 | $1.45\pm0.21$ |
| Mixture of monosialo/disialo/ trisialo gangliosides (1:1:1 w/w/w) | 3 | $1.32\pm0.19$ |
| Mixture of monosialo/disialo/ trisialo gangliosides (1:1:1 w/w/w) | 3 | $1.37\pm0.14$ |
| Mixture of monosialo/disialo/ trisialo gangliosides (1:1:1 w/w/w) | 10 | $2.10\pm0.60$ |

Effect of Porcine Omental Neutral Lipids and of Their Mixture with Calf Brain Gangliosides on Vascular Perfusion In order to assess the effects of non-polar lipids (neutral lipids) and their mixture with polar lipids (e.g., gangliosides), the following experiment was performed:

Two groups of five animals each were operated and injected daily in the wound area (i.m.) for six days either with a total of approximately 10 gm of hexane extracted porcine omentum neutral lipids (PONL), or with the same amount of PONL containing 10 mg Fetal Calf Brain (Total) Gangliosides (FCBG). The animals were radio-imaged the seventh day. FIG. 7 shows the results. The PONL treated animals exhibited considerably higher $\bar{R}$ values ($\bar{R}=1.79+0.09$) than normal healing animals ($\bar{R}=1.22\pm0.17$). However, the addition of only 10 mg of FCBG in 10 gms of PONL increased dramatically the $\bar{R}$ value to $2.59\pm0.18$ which indicates the presence of an unexpected effect.

The terms and expressions which have been employed are used as terms of description and not on limitation, and there is no intention in the use of such terms and expressions of excluding any equivalents of the features shown and described or portions thereof, it being recognized that various modifications are possible within the scope of the invention.

We claim:

1. A method of improving localized vascular perfusion in mammals comprising administering to a mammal in need of improved localized vascular perfusion a therapeutically effective amount of a composition containing angiogenically effective lipid-containing molecules and a pharmaceutically acceptable carrier.

2. A method as in claim 1, wherein said composition comprises an extract of mammalian omental tissue.

3. A method as in claim 1, wherein said composition comprises gangliosides.

4. A method as in claim 3, wherein said composition is administered intravenously.

5. A method as in claim 3, wherein said composition comprises a mixture of mono-, di-, and tri-sialogangliosides.

6. A method as in claim 5, wherein said mixture comprises mono-, di-, and tri-sialogangliosides in a ratio of 1:1:1 by weight.

7. A method as in claim 3, wherein said composition comprises a mixture of di- and tri-sialogangliosides.

8. A method as in claim 7, wherein said di- and tri-sialogangliosides are in a ratio of 1:2 by weight.

9. A method as in claim 3, wherein said mixture further comprises omental neutral lipids.

10. A method as in claim 1, wherein said composition is administered in an amount up to about 500 mg per kg of body weight of said mammal.

11. A method as in claims 1 or 3, wherein said composition is administered subcutaneously.

12. A method as in claims 1 or 3, wherein said composition is administered intramuscularly.

13. A method as in claim 1, wherein said composition comprises a mixture of mammalian omental extract and gangliosides.

14. A method as in claim 1, wherein said composition is administered to said mammal at a site removed from a site where improved vascular perfusion is desired.

15. A method as in claim 14, wherein said composition is administered to said mammal at a site of traumatized tissue.

* * * * *